United States Patent [19]
Chelius

[11] Patent Number: 6,075,146
[45] Date of Patent: Jun. 13, 2000

[54] PROCESS FOR PREPARING BENZOIC ACID DERIVATIVE INTERMEDIATES AND BENZOTHIOPHENE PHARMACEUTICALS

[75] Inventor: Erik Christopher Chelius, Lafayette, Ind.

[73] Assignee: Eli Lilly and Company, Indianapolis, Ind.

[21] Appl. No.: 09/123,889

[22] Filed: Jul. 28, 1998

Related U.S. Application Data

[62] Division of application No. 09/069,277, Apr. 29, 1998, Pat. No. 5,852,193
[60] Provisional application No. 60/045,162, Apr. 30, 1997.
[51] Int. Cl.$^7$ ............ C07D 207/06; C07D 211/06; C07D 223/04; C07D 265/30; C07D 303/00
[52] U.S. Cl. ............ 546/248; 540/609; 540/610; 544/158; 544/171; 548/573; 548/574; 558/48; 560/227
[58] Field of Search ............ 540/609, 610; 544/158, 171; 546/248; 548/573, 574; 558/48; 560/227

[56] References Cited

U.S. PATENT DOCUMENTS

| | | | |
|---|---|---|---|
| 3,394,125 | 7/1968 | Crenshaw | 260/326.5 |
| 3,413,305 | 11/1968 | Crenshaw | 260/326.5 |
| 3,813,396 | 5/1974 | Yale et al. | 260/268 |
| 4,133,814 | 1/1979 | Jones et al. | 260/326 |
| 4,358,593 | 11/1982 | Jones et al. | 546/202 |
| 4,380,635 | 4/1983 | Peters | 546/202 |
| 4,418,068 | 11/1983 | Jones et al. | 424/267 |
| 5,223,510 | 6/1993 | Gubin et al. | 514/299 |
| 5,250,546 | 10/1993 | Masaki et al. | 514/331 |
| 5,319,076 | 6/1994 | Hasegawa et al. | 536/4.1 |
| 5,395,842 | 3/1995 | Labrie et al. | 514/320 |
| 5,470,854 | 11/1995 | Angerer et al. | 514/233 |
| 5,472,962 | 12/1995 | Sagamihara et al. | 514/233.5 |
| 5,482,949 | 1/1996 | Black et al. | 514/324 |
| 5,552,412 | 9/1996 | Cameron et al. | 514/317 |
| 5,629,425 | 5/1997 | Labell et al. | 546/202 |

FOREIGN PATENT DOCUMENTS

| | | |
|---|---|---|
| 0062503 | 10/1982 | European Pat. Off. . |
| 0062504 | 10/1982 | European Pat. Off. . |
| 605 193 | 7/1994 | European Pat. Off. . |
| 64-50872 | 2/1989 | Japan . |
| 2097392 | 4/1982 | United Kingdom . |
| 2096608 | 10/1982 | United Kingdom . |
| 2097788 | 11/1982 | United Kingdom . |
| WO93/10741 | 6/1993 | WIPO . |
| WO95/10513 | 4/1995 | WIPO . |

OTHER PUBLICATIONS

Fujii, Chemical Abstract CA51:424d, 1951.
CAPLUS printout of Gubin et al., Benzofuran Series, Eur. J. Med. Chem., vol. 9, No. 1, pp. 19–25, 1974.
CAPLUS printout of Balogh et al., Synthesis of Oxinazin [1–benzyl–3(3'–dimethylaminopropoxy)–1H–indazole hdyrochloride] a New Antiphlogistic Agent, Acta Pharm. Hung., vol. 44, No. 11–2, pp. 49–52, 1974.
CAPLUS printout of Zikolova et al., Synthesis of Methanesulfonic Acid Esters of Amino Alcohols With Possible Anticancer Activity, Farmatsiya, vol. 17, No. 6, pp. 6–10, 1967.
Jones, C.D., et al, *J. Med. Chem.* 27(8)1057–1066 (1971).
Romeo Wagner, *Synthetic Organic Chemistry*, (171–172) (1953).
Jones, C.D., et al *J. Med Chem.* 35(5) 931–938 1992.
Kym, R.P. et al, *J. Med. Chem.*, 36 (24), 3911–3921 (1993).
Jackson, T.G., et al *J. Chem. Soc.* 1728–1729 (1969).
Kametani, et al *J. Org. Chem. 41* (15) 2545–2547 (1976).
Crenshaw, R.R., et al *J. Med. Chem.* 14(12) 1185–1190 (1971).

*Primary Examiner*—Richard L. Raymond
*Assistant Examiner*—Brenda Coleman
*Attorney, Agent, or Firm*—Gilbert T. Voy

[57] ABSTRACT

The invention relates to intermediates and processes for producing benzothiophenes employing hydroxylamines.

3 Claims, No Drawings

PROCESS FOR PREPARING BENZOIC ACID DERIVATIVE INTERMEDIATES AND BENZOTHIOPHENE PHARMACEUTICALS

CROSS-REFERENCE TO RELATED APPLICATIONS

This application is a divisional of Application Ser. No. 09/069,277, filed Apr. 29, 1998, now U.S. Pat. No. 5,852,193, which claims priority to provisional application Ser. No. 60/045,162, filed Apr. 30, 1997.

BACKGROUND OF THE INVENTION

The present invention relates to the field of pharmaceutical chemistry and relates to a process for preparing benzoic acid derivatives as intermediates in the synthesis of benzothiophenes.

Compounds of formula I

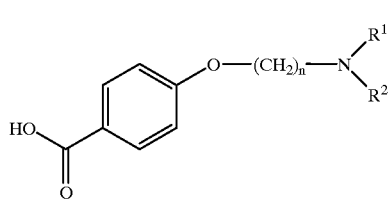

may be prepared by reacting, for example,β-chloroethylpiperidine hydrochloride and ethyl 4-hydroxybenzoate in methyl ethyl ketone, in the presence of potassium carbonate (see, for example, U.S. Pat. No. 4,418,068).

Another synthetic route for preparing a compound of formula I may be found in U.S. Pat. No. 5,631,369, issued May 20, 1997, which employs an alkyl acetate solvent and a base.

However, a more efficient and less expensive process for preparing a compound of formula I, useful in the synthesis of benzothiophenes, would be a significant contribution to the art.

SUMMARY OF THE INVENTION

The present invention relates to a compound of formula VI

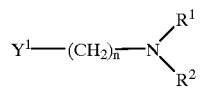

wherein:
R$^1$ and R$^2$ each are independently C$_1$–C$_4$ alkyl, or R$^1$ and R$^2$ together with the nitrogen to which they are attached form a piperidinyl, pyrrolidinyl, methylpyrrolidLnyl, dimethylpyrrolidinyl, morpholiro, dimethylamino, diethylamino, or 1-hexamethyleneimino ring;
n is 2 or 3; and
Y$^1$ is p-toluenesulfonyl-O—, methylsulfonyl-O— trifluoromethylsulfonyl-O—, 2,2,2-trifluoroethylsulfonyl-O—, or trifluoroacetyl-O—; or a salt or solvate thereof.

DETAILED DESCRIPTION OF THE INVENTION

The present invention further relates to a process for preparing compounds of formula VI

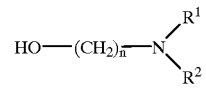

wherein:
R$^1$ and R$^2$ each are independently C$_1$–C$_4$ alkyl, or R$^1$ and R$^2$ together with the nitrogen to which they are attached form a piperidinyl, pyrrolidinyl, methylpyrrolidinyl, dimethylpyrrolidinyl, morpholino, dimethylamino, diethylamino, or 1-hexamethyleneimino ring;
n is 2 or 3; and
Y$_1$ is p-toluenesulfonyl-O—, methylsulfonyl-O—, trifluoromethylsulfonyl-O—, 2,2,2-trifluoroethylsulfonyl-O—, or trifluoroacetyl-O—; or a salt or solvate thereof, comprising reacting a hydroxylamine of formula III

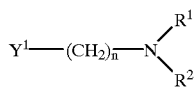

with a compound selected from the group consisting of W$_2$O, and W-halo; wherein W is selected from the group Consisting of p-toluenesulfonyl, methylsulfonyl, trifluoromethylsulfonyl, 2,2,2-trifluoroethylsulfonyl, and trifluoroacetyl.

The present invention also relates to a process for preparing compounds of formula I(a)

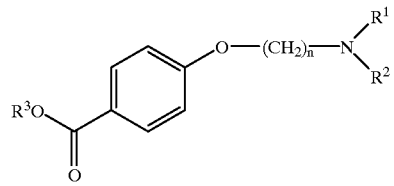

wherein:
R$^1$ and R$^2$ each are independently C$_1$–C$_4$ alkyl, or R$^1$ and R$^2$ together with the nitrogen to which they are attached form a piperidinyl, pyrrolidinyl, methylpyrrolidinyl, dimethylpyrrolidinyl, morpholino, dimethylamino, diethylamino, or 1-hexamethyleneimino ring;
R$^3$ is hydrogen or a carboxy protecting group; and
n is 2 or 3; or a salt or solvate thereof, comprising the step of reacting a hydroxylamine of formula III

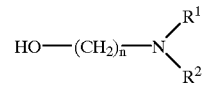

with a compound selected from the group consisting of halogenating reagent, W$_2$O, and W-halo;
wherein
W is selected from the group consisting of p-toluenesulfonyl, methylsulfonyl, trifluoromethylsulfonyl, 2,2,2-trifluoroethylsulfonyl, and trifluoroacetyl; to provide a compound of formula III(a)

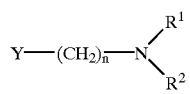

wherein Y is p-toluenesulfonyl-O—, methylsulfonyl-O—, trifluoromethylsulfonyl-O—, 2,2,2-trifluoroethylsulfonyl-O—, trifluoroacetyl-O—, or halo; wherein the compound of formula III(a) is not substantially isolated or purified prior to further reacting the compound of formula IIIa with a compound of formula IV

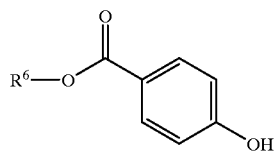

wherein $R^6$ is a carboxy protecting group, in the presence of an alkyl acetate solvent and a suitable base.

The present invention also relates to the preparation of benzothiophenes, and in particular, raloxifene hydrochloride.

General terms used in description of chemical formulae herein bear their usual meanings. For example, the term "$C_1$–$C_4$ alkyl" refers to straight or branched chains of 1 to 4 carbon atoms including, methyl, ethyl, propyl, isopropyl, butyl, n-butyl, and isobutyl; and the term "$C_1$–$C_6$ alkyl" encompasses the groups included in the definition of "$C_1$–$C_4$ alkyl" in addition to groups such as pentyl, isopentyl, hexyl, isohexyl, and the like. The term "lower alcohols" refers to $C_1$–$C_4$ alcohols including methanol, ethanol, propanol, isopropanol, butanol, n-butanol, isobutanol, and the like. The term "halo" includes bromo, chloro, fluoro, and iodo.

The term "halogenating agent" refers to a reagent that will donate a halogen to the target molecule.

Typical halogenating reagents include but are not limited to benzeneseleninylchloride/aluminum chloride, thionyl bromide, thionyl chloride, oxalyl chloride, N-bromo-succinimide, N-iodo-succinimide, N-chlorosuccinimide, molecular chlorine, molecular bromine, molecular iodine, and the like. Thionyl chloride is a preferred halogenating reagent.

The term "Lewis acid catalyst" refers to the type of catalyst described in Olah, "Friedel-Crafts and Related Reactions," Interscience Publishing Co., New York, 1963 and includes metal halides such as aluminum bromide, aluminum chloride, boron trifluoride, boron trichloride, boron tribromide, titanium tetrachloride, titanium tetrabromide, stannic chloride, stannic bromide, bismuth trichloride, ferric chloride and the like.

The term "hydroxy protecting group" denotes a group understood by one skilled in the organic chemical arts of the type described in Chapter 2 of "Protective Groups in Organic Synthesis, 2nd Edition, T. H. Greene, et al., John Wiley & Sons, New York, 1991, hereafter "Greene".

Representative hydroxy protecting groups include, for example —$C_1$–$C_4$ alkyl, —CO—($C_1$–$C_6$ alkyl), —$SO_2$—($C_4$–$C_6$ alkyl), and —CO—Ar in which Ar is optionally substituted phenyl. More specifically, other hydroxy protecting groups include, for example ether groups including methyl and substituted methyl ether groups such as methyl ether, methoxymethyl ether, methylthiomethyl ether, tert-buylthiomethyl ether, (phenyldimethylsilyl)methoxymethyl ether, benzyloxymethyl ether, p-methoxy-benzyloxymethyl ether, and tert-butoxy-methyl ether; substituted ethyl ether groups such as ethoxyethyl ether, 1-(2-chloroethoxy)ethyl ether, 2,2,2-trichloroethoxymethyl ether, and 2-(trimethylsilyl)ethyl ether; isopropyl ether groups; phenyl and substituted phenyl ether groups such as phenyl ether, p-chlorophenyl ether, p-methoxyphenyl ether, and 2,4-dinitrophenyl ether; benzyl and substituted benzyl ether groups such as benzyl ether, p-methoxybenzyl ether, o-nitrobenzyl ether, and 2,6-dichlorobenzyl ether; and alkylsilyl ether groups such as trimethyl- triethyl- and triisopropylsilyl ethers, mixed alkylsilyl ether groups such as dimethylisopropylsilyl ether, and diethylisopropylsilyl ether; and ester protecting groups such as formate ester, benzylformate ester, mono- di- and trichloroacetate esters, phenoxyacetate ester, and p-chlorophenoxyacetate and the like. The species of hydroxy protecting group employed is not critical so long as the derivatized hydroxy group is stable to the condition of subsequent reaction(s) on other positions of the intermediate molecule and can be selectively removed at the appropriate point without disrupting the remainder of the molecule including any other hydroxy protecting group(s). It is within the knowledge of one skilled in the art to select appropriate hydroxy protecting group(s) for a given set of reaction conditions given the guidance provided by Greene cited above. A preferred embodiment of this invention is where $R^4$ and $R^5$, in compounds of formula II and V, are both methyl.

The term "carboxy protecting group" as used in this specification refers to one of the ester derivatives of the carboxylic acid group commonly employed to block or protect the carboxylic acid group while reactions are carried out on other functional groups of the compound. Examples of such carboxylic acid protecting groups include benzyl, benzyhydryl, $C_1$–$C_6$ alkyl, and tri ($C_1$–$C_4$ alkyl)silyl. Futher examples of these groups are found in E. Haslam, "Protective Groups in Organic Chemistry", J. G. W. McOmie, Ed., Plenum Press, New York, N.Y., 1981, Chapter 5. Preferred carboxylic acid protecting groups are $C_1$–$C_6$ alkyl groups.

The term "acyl activating group" refers to a substituent to a carbonyl that promotes nucleophilic addition reactions to the carbonyl. Suitable activating substituents are those which have a net electron withdrawing effect on the carbonyl. Typical electron withdrawing groups include groups that when combined with the carbonyl form an ester or amide. Such groups include hydroxybenzotriazole, imidazole, a nitrophenol, pentachlorophenol, N-hydroxysuccinimide, dicyclohexylcarbodiimide, N-hydroxy-N-methoxyamine, and the like. The term acyl activating group also encompasses groups that when combined with the carbonyl form an acid anhydride. Such groups include, but are not limited to small carboxylic acids such as acetic, formic, sulfonic, methanesulfonic, ethanesulfonic, benzenesulfonic, or p-tolylsulfonic acid, and the like. Furthermore, a halogen attached to carbonyl activates it for nucleophilic addition. Suitable halogens include chloro, bromo, or iodo.

As mentioned above, the instant invention includes the salts of the compounds defined by formulae Ia, II, and VI. Although generally neutral, a compound of formula Ia, II, or VI can possess a sufficiently basic functional group, and accordingly react with any of a number of inorganic and organic acids, to form a salt. A preferred salt for the compounds are those which are pharmaceutically acceptable such that they pose no significant health risk to the ultimate patient. See, for example, Berge, S. M, Bighley, L. D., and Monkhouse, D. C., *J. Pharm. Sci.,* 66, 1, 1977.

Typical inorganic acids used to form such salts include hydrochloric, hydrobromic, hydroiodic, nitric, sulfuric, phosphoric, hypophosphoric, and the like. Salts derived from organic acids, such as aliphatic mono and dicarboxylic acids, phenyl-substituted alkanoic acids, hydroxyalkanoic and hydroxyalkandioic acids, aromatic acids, aliphatic and aromatic sulfonic acids, may also be used. Such pharmaceutically acceptable salts thus include acetate, phenylacetate, trifluoroacetate, acrylate, ascorbate, benzoate, chlorobenzoate, dinitrobenzoate, hydroxybenzoate, methoxybenzoate, methylbenzoate, o-acetoxybenzoate, naphthalene-2-benzoate, bromide, isobutyrate, phenylbutyrate, β-hydroxybutyrate, butyne-1,4-dioate, hexyne-1,4-dioate, caproate, caprylate, chloride, cinnamate, citrate, formate, fumarate, glycolate, heptanoate, hippurate, lactate, malate, maleate, hydroxymaleate, malonate, mandelate, mesylate, nicotinate, isonicotinate, nitrate, oxalate, phthalate, terephthalate, phosphate, monohydrogenphosphate, dihydrogenphosphate, metaphosphate, pyrrophosphate, propiolate, propionate, phenylpropionate, salicylate, sebacate, succinate, suberate, sulfate, bisulfate, pyrosulfate, sulfite, bisulfite, sulfonate, benzenesulfonate, p-bromophenylsulfonate, chlorobenzenesulfonate, ethanesulfonate, 2-hydroxyethanesulfonate, methanesulfonate, naphthalene-1-sulfonate, naphthalene-2-sulfonate, p-toluenesulfonate, xylenesulfonate, tartarate, and the like. A preferred salt is the hydrochloride salt.

The term "suitable acid" refers to any acid reactive enough to affect the desired reaction without significantly affecting any undesired reactions. The skilled artisan will recognize that the reactivity of an acid relates to the ability to donate a proton (Brønsted acidity) or the ability to accept an electron pair (Lewis acidity).

The term "suitable base" refers to any base reactive enough to affect the desired reaction without significantly affecting any undesired reactions. The skilled artisan will recognize that the reactivity of a a base reactivity relates to the ability to donate a hydroxide ion (Brønsted basicity) or the ability to donate an electron pair (Lewis basicity).

The term "suitable solvent" refers to any solvent inert to the ongoing reaction that sufficiently solubilizes the reactants to effect the desired reaction.

The term "alkyl acetate solvents" refers to solvents of the formula $CH_3CO_2$-alkyl, and include those in which the alkyl moiety of such solvent is a straight or branched chain alkyl moiety having one to nine carbon atoms. Illustrative alkyl acetate solvents include, for example, ethyl acetate, propyl acetate, isopropyl acetate, butyl acetate, isoamyl acetate, and the like. The preferred solvent is amyl acetate.

The term "not substantially isolated or purified" refers to compounds that are either produced and then subsequently reacted in situ to form other compounds or compounds that are produced and the reaction solvent may be removed by evaporation or concentration under reduced pressure before use in subsequent reactions.

The starting materials for the processes of the present invention may be obtained by a number of routes, including those disclosed in U.S. Pat. No. 4,418,068, U.S. Pat. No. 4,133,814, and U.S. Pat. No. 4,380,635, the disclosures of which are herein Incorporated by reference. The process for preparing compounds of formula Ia as provided by the instant invention is shown below in Scheme 1 where $R^6$ is a carboxy protecting group. The overall process of the present invention is depicted in Schemes 1 and 2, provided below.

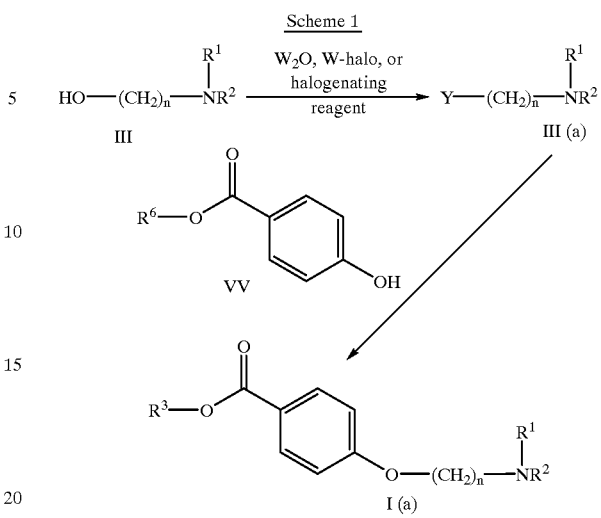

A commercially available compound of formula III may be reacted with a halogenating reagent, or with a compound of the formula $W_2O$ or W-halo, wherein W includes p-toluenesulfonyl, methylsulfonyl, trifluoromethylsulfonyl, trifluoroethanesulfonyl, or trifluoroacetyl, in the presence of a suitable solvent.

A solvent is not necessary when the reaction is run with thionyl chloride. Suitable solvents include organic solvents, such as acetonitrile, chloroform, ethyl acetate, dimethylformamide, tetrahydrofuran, MTBE, toluene, 1,4-dioxane, and the like. A preferred solvent is methylene chloride.

Suitable examples of a halogenating reagent, $W_2O$, or W-halo include p-toluenesulfonylchloride, methylsulfonyl chloride, trifluoromethylsulfonyl chloride, trifluoroacetic anhydride, and the like, Preferred are thionyl chloride, 2,2,2-trifluoroethylsulfonyl chloride, and p-toluenesulfonyl chloride. These compounds are typically employed in a slight molar excess. For example, a 1.01 to 1.3 molar excess, relative to the hydroxylamines of formula III is preferred. The reaction 15 is preferably carried out at about 0° C. –5° C. during the addition, followed by room temperature for about 10 to 14 hours. The product of this reaction is preferably not isolated or purified and instead used directly in the following reaction.

Upon completion of the above reaction, the solvent may be removed and the crude product may be taken directly to the next step where the compound of formula IIIa may be reacted with a 4-hydroxybenzoate of formula IV in the presence of a suitable base and an appropriate alkyl acetate solvent. Suitable alkyl acetate solvents include ethyl acetate, propyl acetate, isopropyl acetate, butyl acetate, isoamyl acetate, and the like. The preferred solvent is amyl acetate. Suitable bases include organic and inorganic bases, but inorganic bases, particularly a carbonate or bicarbonate base, is preferred. Of these, powdered potassium carbonate is especially preferred. The 4-hydroxybenzoate of formula IV is typically employed in a molar deficiency. For example, a 50 to 70 molar percent, relative to the hydroxylamines of formula III, is generally employed. A 58 molar percent is preferred. The base is typically employed in a slight molar excess. For example, a 1.3 to 1.8 molar excess, relative to the hydroxylamines of formula III, is generally employed. A 1.55 molar excess is typically preferred. The present reaction may be run at a temperature from about 80° C. to the reflux temperature of the solvent. A preferred temperature range is from about 100° C. to about 150° C. Typically, this reaction takes from about 2 to about 24 hours.

Upon completion of the above reaction, the alkylation mixture is typically cooled to from about 30° C. to about 70° C., and washed with water to dissolve the basic salt of the compound of formula Ia ester. A suitable acid is then added to form an acid addition salt in order to extract the resulting product. Preferably, aqueous hydrochloric acid is used for the extraction process, which forms a hydrochloride salt of the formula Ia ester. Other aqueous acids, such as those that are listed to prepare pharmaceutically acceptable salts, may be used to extract the compounds of formula Ia ester.

To cleave the $R^3$ ester group (when $R^3$ is not hydrogen), typically the formula Ia acid extract from above is heated to a temperature in the range from about 80° C. to about 150° C., preferably from about 95° C. to about 100° C. At the preferred temperature range, an acceptable level of formula Ia acid compound is produced in about 4 hours. Continued heating for up to 24 hours generally does not affect either quality or yield. Optionally, while applying heat in the above stated temperature range, the ester cleaving may be accelerated by distilling and removing the alcohol formed via acid hydrolysis.

Isolation and purification of the formula Ia acid or ester is accomplished using procedures well known to one of ordinary skill in the art. To purifiy the Ia acid, generally, the resulting mixture from the ester cleavage step is cooled to a temperature range from about −5° C. to about 20° C. Although the product will crystallize or precipitate out of solution at this range, the optimum temperature range is from about 0° C. to about 5° C. The desired formula Ia acid is then isolated by filtration.

Compounds of formula II may be prepared by methods illustrated in Scheme 2 below.

Scheme 2

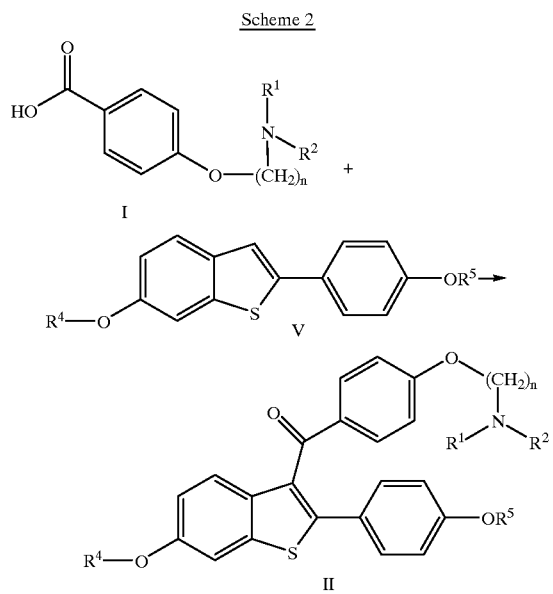

A compound of formula V may then be acylated under Friedel Crafts conditions with a compound of formula I, which was preferably isolated and purified prior to the initiation of this step, in the presence of a Lewis acid catalyst. To perform this reaction, the acid group of the compound ot formula I must first be converted to an acyl activating group by methods well known in the art, and shown in the Examples section below. The resulting compound of formula II may optionally, in the case where $R^4$ and $R^5$ are hydroxy protecting groups, be treated with a suitable acid to give the compounds of formula II where $R^4$ and $R^5$ are both hydrogen.

Compounds of formula V are known in the art and are prepared, for example, as described by Peters in U.S. Pat. No. 4,380,635, or Jones, et al., in U.S. Pat. Nos. 4,133,814 and 4,418,068, the disclosures of which are herein incorporated by reference. Although the $R^4$ and $R^5$ protecting groups are not required for this step, thus allowing a compound of formula V in which $R^4$ and $R^5$ are hydrogen to be acylated with a compound of formula I, one skilled in the art would recognize that a hydroxy protecting group, particularly methyl, is preferred. A preferred formula I compound for the present acylation reaction is one in which $R^1$ and $R^2$ together with the nitrogen to which they are attached form a piperidinyl ring, and n is 2.

Reagents and all parameters necessary to carry out the acylation step, the optional deprotection step, the optional salt formation step, and isolation and purification of formula II compounds are described in the United States patents provided above. Thus, pharmaceutically active compounds of formula II, including their acid addition salts, are prepared via the instant process of the present invention.

In general, the reactions of Synthetic Schemes 1–2 are substantially complete in about 15 minutes to 72 hours when conducted at a temperature range of from about 0° C. to the reflux temperature of the reaction mixture. The optimal time for performing the reactions of the invention can be determined by monitoring the progress of the reaction via conventional chromatographic techniques. Furthermore, it is preferred to conduct the reactions of the invention under an inert atmosphere, such as, for example, argon, or, particularly, nitrogen. Although the compounds of formula I are preferably isolated and purified before use in subsequent reactions, the compounds of formula IIIa are preferably not isolated and purified before use in subsequent reactions. Compounds of formula I may be crystallized and then collected by filtration as described above, or the reaction solvent may be removed by extraction, evaporation, or decantation. The intermediate may be further purified, if desired by common techniques such as recrystallization or chromatography over solid supports such as silica gel or alumina.

The following Examples are provided to better elucidate the practice of the present invention and should not be interpreted in any way as to limit the scope of same. Those skilled in the art will recognize that various modifications may be made while not departing from the spirit and scope of the invention. All publications and patent applications mentioned in the specification are indicative of the level of those skilled in the art to which this invention pertains.

EXAMPLES

Preparation 1

4-(2-piperidinoethoxy) benzoic acid hydrochloride

Into a 500 ml round bottom flask is placed 23.38 g (197 mmol) of thionyl chloride and 140 ml of methylene chloride. The resulting solution is cooled with an ice bath as 21.91 g (170 mmol) of 1-piperidinoethanol in 30 ml of methylene chloride is added over 30 minutes. After the addition is complete, the ice bath is removed and the mixture is stirred for about 12 hours. The reaction mixture is concentrated on a rotary evaporator to yield a solid residue. Amyl acetate (225 ml), potassium carbonate (34.4 g, 249 mmol), and methyl 4-hydroxybenzoate (14.1 g, 92 mmol) are added to the residue. The resulting slurry is heated to 135° C. for 5 hours. The reaction mixture is cooled to room temperature and washed twice with 100 ml of water. The organic layer is extracted with 53 ml of 8 N hydrochloric acid. The aqueous layer is heated at gentle reflux for 4 hours. The resulting slurry is cooled to 50° C. and 50 ml of acetone is added. The slurry is cooled to 0–5° C. and stirred for 1 hour. The product is filtered, washed with cold acetone, and dried at 50° C. in vacuo to yield 17.9 g of product, (67%). $^1$H NMR. Compares to reference solution: HPLC potency 97.9%, TRS 1.50% .

Preparation 2

4-(2-piperidinoethoxy) benzoic acid hydrochloride

Into a 50 ml round bottom flask is placed 6.40 g (33.6 mmol) of p-toluenesulfonyl chloride and 25 ml of methylene chloride. The resulting solution is cooled with an ice bath as 4.00 g (31.0 mmol) of 1-piperidinoethanol in 6 ml of methylene chloride is added dropwise. After the addition is complete, the ice bath is removed and the resulting slurry is stirred for about 12 hours. The reaction mixture is concentrated on a rotary evaporator to yield a solid residue. The solid residue is transferred to a 100 ml round bottom flask with 45 ml of amyl acetate. Potassium carbonate (6.87 g, 49.7 mmol) and methyl 4-hydroxybenzoate (2.82 g, 18.5 mmol) are added to the slurry. The resulting mixture is heated to 145° C. for 2 hours. The reaction mixture is cooled to room temperature and washed twice with water. The organic layer is extracted with 11 ml of 8 N hydrochloric acid. The aqueous layer is heated at gentle reflux for 3 hours. The resulting slurry is cooled to 50° C. and 11 ml of acetone is added. The slurry is cooled to 0–5°0 C. and stirred for 1 hour. The product is filtered, washed with cold acetone, and dried at 50° C. in vacuo to yield 920 mg of product, (17%). $^1$H NMR. Potency 97.6%. TRS 1.16%

Preparation 3

4-(2-piperidinoethoxy) benzoic acid hydrochloride

Into a 50 ml round bottom flask is placed 4.93 g (27.0 mmol) of 2,2,2-trifluoroethanesulfonyl chloride and 25 ml of methylene chloride. The resulting solution is cooled with an ice bath as 3.22 g (24.9 mmol) of 1-piperidinoethanol in 7 ml of methylene chloride is added dropwise. After the addition is complete, the ice bath is removed and the resulting slurry is stirred for about 12 hours. The reaction mixture is concentrated on a rotary evaporator to yield a waxy residue. The solid residue is slurried in 45 ml of amyl acetate and then potassium carbonate (5.50 g, 39.9 mmol) and methyl 4-hydroxybenzoate (2.26 g, 14.8 mmol) are added. The resulting mixture is heated to 140° C. for 2 hours. The reaction mixture is cooled to room temperature and washed twice with water and the organic layer is extracted with 10.5 ml of 8 N hydrochloric acid. The aqueous layer is heated at gentle reflux for 4 hours. The resulting slurry is cooled to 50° C. and 11 ml of acetone is added. The slurry is cooled to 0–5° C. and stirred for 1 hour. The product is filtered, washed with cold acetone, and dried at 50° C. in vacuo to yield 3.94 g of product, (90%). $^1$H NMR. HPLC 96.9%. TRS 2.78%.

Example 1

[16-hydroxy-2-(4-hydroxyphenyl)-3-[4-(2-piperidinoethoxy)benzyl]benzo[b]thiophene hydrochloride]

A solution of 4-(2-piperidinoethoxy) benzoic acid hydrochloride (30.01 g) and dimethylformamide (2 mL) in methylene chloride (500 mL) is treated with oxalyl chloride (10.5 mL) over a 30–35 minute period. After stirring for about 18 hours, the reaction is assayed for completion by HPLC analysis. Additional oxalyl chloride may be added to the reaction if the starting carboxylic acid is present. Upon completion, the reaction solution is evaporated to dryness in vacuo. The residue was dissolved in methylene chloride (200 mL), and the resulting solution evaporated to dryness. The dissolution/evaporation procedure is repeated and 6-methoxy-2-(4-methoxyphenyl) benzo[b]thiophene (25.4 g), and 1,2-dichloroethane (450 mL) is added and the reaction is cooled to 0° C. Boron trichloride gas is condensed into a cold graduated cylinder (24.4 mL), and added to the cold mixture described above. After 8 hours at 0° C., the reaction mixture is treated with additional boron trichloride gas (24.4 mL). The resulting solution is heated to 35° C. After 16 hours the reaction is complete. Methanol (250 mL) is added to the reaction mixture over about 20 minutes, causing the methanol to reflux. The resulting slurry is stirred at 25° C. After 1 hour, the crystalline prouduct was filtered, washed with cold methanol (64 mL), and dried at 40° C. in vacuo to give the title compound. m.p. 225° C. HPLC.

I claim:
1. A compound of formula VI

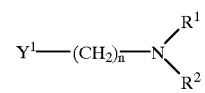

VI wherein

R$^1$ and R$^2$ each are independently C$_1$–C$_4$ alkyl, or R$^1$ and R$^2$ together with the nitrogen to which they are attached form a piperidinyl, pyrrolidinyl, methylpyrrolidinyl, dimethylpyrrolidinyl, morpholino, dimethylamino, diethylamino, or 1-hexamethyleneimino ring;

n is 2 or 3; and

Y$^1$ is 2,2,2-trifluoroethylsulfonyl-O—; or a salt or solvate thereof.

2. A compound according to claim 1 wherein n is 2.

3. A compound according to claim 1 wherein R$^1$ and R$^2$ together with the nitrogen to which they are attached form a piperidinyl ring.

* * * * *